(12) United States Patent
Murray et al.

(10) Patent No.: US 12,383,700 B2
(45) Date of Patent: Aug. 12, 2025

(54) REUSABLE URINARY CATHETER PRODUCTS

(71) Applicant: Hollister Incorporated, Libertyville, IL (US)

(72) Inventors: Michael G. Murray, Ballina (IE); Horacio Montes De Oca, Ballina (IE); Gary W. Inglese, Deerfield, IL (US); Rebecca M. Leece, Bicester (IE); Darcy R. Balaski, Castlebar (IE); John T. Clarke, Galway (IE); John P. O'Mahony, Ardnacrusha (IE); Dmitry Sheremetiev, Oranmore (IE); Denise Gamblin, Leeds (GB); Thomas Renehan, Ballina (IE); Richard J. Meaney, Westport (IE); Vivienne McNulty, Dublin (IE)

(73) Assignee: Hollister Incorporated, Libertyville, IL (US)

( * ) Notice: Subject to any disclaimer, the term of this patent is extended or adjusted under 35 U.S.C. 154(b) by 432 days.

(21) Appl. No.: 17/616,598

(22) PCT Filed: Jun. 10, 2020

(86) PCT No.: PCT/US2020/036969
§ 371 (c)(1),
(2) Date: Dec. 3, 2021

(87) PCT Pub. No.: WO2020/252003
PCT Pub. Date: Dec. 17, 2020

(65) Prior Publication Data
US 2022/0241549 A1  Aug. 4, 2022

Related U.S. Application Data

(60) Provisional application No. 62/861,130, filed on Jun. 13, 2019.

(51) Int. Cl.
*A61M 25/00* (2006.01)

(52) U.S. Cl.
CPC ...... *A61M 25/002* (2013.01); *A61M 25/0045* (2013.01); *A61M 2025/0019* (2013.01); *A61M 2025/0046* (2013.01)

(58) Field of Classification Search
CPC ............ A61M 25/002; A61M 25/0017; A61M 25/0046; A61M 2025/0019; A61M 25/02; A61B 50/30; A61B 2050/3005
See application file for complete search history.

(56) References Cited

U.S. PATENT DOCUMENTS

| 1,120,549 | A | 12/1914 | Schellberg |
| 3,794,042 | A | 2/1974 | De Klotz et al. |

(Continued)

FOREIGN PATENT DOCUMENTS

| BR | 201400709 A2 * | 12/2015 |
| DE | 3819257 C1 | 7/1989 |

(Continued)

OTHER PUBLICATIONS

International Search Report and Written Opinion Dated Oct. 9, 2020 for International Application No. PCT/US2020/036969.

*Primary Examiner* — Nicholas J. Weiss
*Assistant Examiner* — Linnae E. Raymond
(74) *Attorney, Agent, or Firm* — Cook Alex Ltd.

(57) ABSTRACT

A reusable urinary catheter (72), comprising a catheter tube (12), a drainage member (22), the proximal end portion of the drainage member being connected to the distal end of the catheter tube, the distal end portion of the drainage member defining a drainage opening (28); a collapsible sleeve (18) surrounding the catheter tube, an introducer attached to the proximal end portion of the sleeve and the distal end portion of the sleeve being attached to the drainage member, the (Continued)

drainage member including channels (23) in fluid communication with the interior cavity of the sleeve, the channels allowing passage of sterilization fluid into and out of the sleeve; a holder (74) having a first port (66) and a second port (68), the introducer being releasably attached to the first port and the drainage member being releasable attached to the second port; and a sterilization fluid located within the sleeve.

18 Claims, 11 Drawing Sheets

(56) References Cited

U.S. PATENT DOCUMENTS

| | | |
|---|---|---|
| 3,956,011 A | 5/1976 | Carleton |
| 4,170,996 A | 10/1979 | Wu |
| 4,346,706 A | 8/1982 | Leveen |
| 4,754,877 A | 7/1988 | Johansson et al. |
| 5,120,322 A | 6/1992 | Davis |
| 5,207,705 A | 5/1993 | Trudell |
| 5,226,530 A | 7/1993 | Golden |
| 5,292,802 A | 3/1994 | Rhee |
| 5,369,131 A | 11/1994 | Poli |
| 5,451,406 A | 9/1995 | Lawin |
| 5,718,862 A | 2/1998 | Thompson |
| 5,800,412 A | 9/1998 | Zhang |
| 6,113,629 A | 9/2000 | Ken |
| 6,129,956 A | 10/2000 | Morra |
| 6,352,710 B2 | 3/2002 | Sawhney |
| 6,387,080 B1 | 5/2002 | Rødsten |
| 6,409,723 B1 | 6/2002 | Edwards |
| 6,419,673 B1 | 7/2002 | Edwards |
| 6,524,608 B2 | 2/2003 | Ottoboni |
| 6,535,768 B1 | 3/2003 | Baker |
| 6,548,487 B2 | 4/2003 | Takahashi |
| 6,607,525 B2 | 8/2003 | Franco |
| 6,695,831 B1 | 2/2004 | Tsukada et al. |
| 7,014,861 B2 | 3/2006 | Roorda |
| 7,125,858 B2 | 10/2006 | Filion |
| 7,235,107 B2 | 6/2007 | Evans |
| 7,390,525 B2 | 6/2008 | Epstein |
| 7,537,589 B2 | 5/2009 | Tsukada et al. |
| 7,767,652 B2 | 8/2010 | Hendriks |
| 7,857,804 B2 | 12/2010 | McCaffrey |
| 7,862,552 B2 | 1/2011 | McIntyre |
| 7,918,819 B2 | 4/2011 | Karmarkar |
| 7,976,847 B2 | 7/2011 | Southard |
| 8,158,187 B2 | 4/2012 | Chen |
| 8,163,326 B2 | 4/2012 | Zhong |
| 8,235,937 B2 | 8/2012 | Palasis |
| 8,252,738 B2 | 8/2012 | Marx |
| 8,267,919 B2 | 9/2012 | Utas |
| 8,461,104 B2 | 6/2013 | Bengmark |
| 8,580,551 B2 | 11/2013 | Kaplan |
| 8,585,753 B2 | 11/2013 | Scanlon |
| 8,617,542 B2 | 12/2013 | Madhyastha |
| 8,646,445 B2 | 2/2014 | Fine |
| 8,680,228 B2 | 3/2014 | Guo |
| 8,685,427 B2 | 4/2014 | Li |
| 8,703,180 B1 | 4/2014 | Stankus |
| 8,709,465 B2 | 4/2014 | Chen |
| 8,889,211 B2 | 11/2014 | Owens |
| 8,911,424 B2 | 12/2014 | Weadock |
| 8,916,227 B2 | 12/2014 | Horres |
| 8,933,416 B2 | 1/2015 | Arcand et al. |
| 9,132,151 B2 | 9/2015 | Ko |
| 9,226,926 B2 | 1/2016 | Ueda |
| 9,295,663 B2 | 3/2016 | Pacetti |
| 9,364,513 B2 | 6/2016 | Ellis-Behnke |
| 9,415,084 B2 | 8/2016 | Ellis-Behnke |
| 9,724,448 B2 | 8/2017 | Kobayashi |
| 9,884,028 B2 | 2/2018 | Holzer |
| 10,076,537 B2 | 9/2018 | Marcum |
| 10,137,287 B2 | 11/2018 | Sansone |
| 10,172,978 B2 | 1/2019 | Wedlin |
| 10,227,718 B2 | 3/2019 | Cahil |
| 10,232,143 B2 | 3/2019 | Rajagopalan |
| 10,525,172 B2 | 1/2020 | Martin |
| 10,532,132 B2 | 1/2020 | Tobias |
| 10,537,375 B2 | 1/2020 | Wang |
| 10,583,237 B2 | 3/2020 | Feld |
| 10,639,400 B2 | 5/2020 | Sartor |
| 10,695,461 B2 | 6/2020 | Suppiger |
| 10,791,735 B2 | 10/2020 | Thomas |
| 10,806,830 B2 | 10/2020 | Wang |
| 10,829,520 B2 | 11/2020 | Obrecht |
| 10,849,324 B2 | 12/2020 | Sawyer |
| 10,987,208 B2 | 4/2021 | Schaefer |
| 11,001,612 B2 | 5/2021 | Zlotkin |
| 11,001,688 B2 | 5/2021 | Niu |
| 11,098,203 B2 | 8/2021 | Ozcelik |
| 11,541,205 B2 | 1/2023 | Erbey, II |
| 2002/0058631 A1 | 5/2002 | Cai |
| 2003/0017073 A1 | 1/2003 | Eckhardt et al. |
| 2003/0130228 A1 | 7/2003 | Chen |
| 2003/0181388 A1 | 9/2003 | Cai |
| 2003/0191064 A1 | 10/2003 | Kopke |
| 2004/0005423 A1 | 1/2004 | Dalton |
| 2004/0047892 A1 | 3/2004 | DesRosiers |
| 2004/0049134 A1 | 3/2004 | Tosaya |
| 2004/0092821 A1 | 5/2004 | Hering |
| 2004/0151702 A1 | 8/2004 | Marksteiner |
| 2004/0197784 A1 | 10/2004 | Miano |
| 2004/0215231 A1 | 10/2004 | Fortune |
| 2005/0003010 A1 | 1/2005 | Cohen |
| 2005/0013812 A1 | 1/2005 | Dow |
| 2005/0033374 A1 | 2/2005 | Gerber |
| 2005/0163818 A1 | 7/2005 | Sung |
| 2006/0025753 A1* | 2/2006 | Kubalak ............ A61M 25/0111 604/327 |
| 2006/0093644 A1 | 5/2006 | Quelle |
| 2006/0134186 A1 | 6/2006 | Carlton |
| 2007/0066963 A1 | 3/2007 | Tanghoj |
| 2007/0239107 A1 | 10/2007 | Lundberg |
| 2008/0091145 A1 | 4/2008 | House |
| 2008/0103481 A1 | 5/2008 | Vogel |
| 2008/0177217 A1 | 7/2008 | Polaschegg |
| 2008/0200907 A1 | 8/2008 | Nestenborg |
| 2008/0200924 A1 | 8/2008 | Burbank |
| 2008/0242614 A1 | 10/2008 | Fraser |
| 2008/0275015 A1 | 11/2008 | Potter |
| 2008/0311172 A1 | 12/2008 | Schapira |
| 2009/0071851 A1 | 3/2009 | Maki et al. |
| 2009/0098187 A1 | 4/2009 | Peters |
| 2009/0101531 A1 | 4/2009 | Nordholm et al. |
| 2009/0171317 A1 | 7/2009 | Versi |
| 2009/0227981 A1 | 9/2009 | Bennett |
| 2009/0299334 A1 | 12/2009 | Nishtala et al. |
| 2010/0198195 A1 | 8/2010 | Nishtala |
| 2010/0331819 A1 | 12/2010 | Hossainy |
| 2011/0091515 A1 | 4/2011 | Zilberman |
| 2011/0114520 A1 | 5/2011 | Matthison-Hansen |
| 2011/0137296 A1 | 6/2011 | Tanghoj |
| 2011/0142901 A1 | 6/2011 | Brandon |
| 2012/0168324 A1 | 7/2012 | Carleo |
| 2012/0179145 A1 | 7/2012 | Nishtala |
| 2012/0245518 A1 | 9/2012 | Lovasz |
| 2012/0316515 A1 | 12/2012 | Terry |
| 2013/0267888 A1 | 10/2013 | Rhodes et al. |
| 2014/0236082 A1 | 8/2014 | Roorda |
| 2014/0264074 A1 | 9/2014 | Victor et al. |
| 2014/0316380 A1* | 10/2014 | Davis ................... A61M 25/00 604/523 |
| 2015/0367029 A1 | 12/2015 | DeVore |
| 2016/0331841 A1 | 11/2016 | Prestwich |
| 2017/0065519 A1 | 3/2017 | Zilberman |
| 2017/0106120 A1 | 4/2017 | McClendon |
| 2017/0136127 A1 | 5/2017 | Maki |
| 2017/0165194 A1 | 6/2017 | Meng |
| 2018/0169377 A1* | 6/2018 | Hickmott ......... A61M 25/0097 |
| 2018/0207323 A1 | 7/2018 | Chen |
| 2018/0236141 A1 | 8/2018 | Russell |

(56) References Cited

U.S. PATENT DOCUMENTS

| | | |
|---|---|---|
| 2018/0338475 A1 | 11/2018 | Ala'Aldeen et al. |
| 2019/0030184 A1 | 1/2019 | Kidambi |
| 2019/0046488 A1 | 2/2019 | Rosenblatt |
| 2019/0175104 A1 | 6/2019 | Malik |
| 2019/0262500 A1 | 8/2019 | Xu |
| 2019/0269816 A1 | 9/2019 | Williams |
| 2019/0328915 A1* | 10/2019 | Paul .................... A61L 2/085 |
| 2019/0375149 A1 | 12/2019 | Limem |
| 2020/0001049 A1* | 1/2020 | House ............... A61M 25/0111 |
| 2020/0009214 A1 | 1/2020 | Gil |
| 2020/0056063 A1 | 2/2020 | Wilson |
| 2020/0190511 A1 | 6/2020 | Olson |
| 2020/0197562 A1 | 6/2020 | Xue |
| 2020/0368159 A1 | 11/2020 | Chen |
| 2020/0392465 A1 | 12/2020 | Sanghavi |
| 2021/0015993 A1 | 1/2021 | O'Neill |
| 2021/0145749 A1 | 5/2021 | Tagil |
| 2021/0275727 A1* | 9/2021 | Farrell ............... A61M 25/0009 |
| 2022/0016398 A1 | 1/2022 | Li |
| 2022/0054295 A1* | 2/2022 | Becker ................... A61F 5/451 |
| 2022/0233437 A1 | 7/2022 | Borody |
| 2022/0257843 A1 | 8/2022 | Testani |
| 2022/0273587 A1 | 9/2022 | Parsons |
| 2022/0273698 A1 | 9/2022 | Lovasz |
| 2022/0280682 A1 | 9/2022 | Bodkhe |
| 2022/0370688 A1 | 11/2022 | Sileika |

FOREIGN PATENT DOCUMENTS

| | | | |
|---|---|---|---|
| DE | 10334372 A1 * | 2/2005 | .......... A61M 25/002 |
| DE | 102004013712 B3 | 8/2005 | |
| EP | 0751796 A1 | 1/1997 | |
| EP | 0887373 A2 | 12/1998 | |
| EP | 1087795 A1 | 4/2001 | |
| EP | 1181023 B1 | 2/2002 | |
| EP | 1060204 B1 | 6/2002 | |
| EP | 1214038 A2 | 6/2002 | |
| EP | 1070502 B1 | 6/2003 | |
| EP | 1324785 B1 | 4/2004 | |
| EP | 1589888 A2 | 11/2005 | |
| EP | 1272227 B1 | 4/2006 | |
| EP | 1264613 B1 | 2/2007 | |
| EP | 1682124 B1 | 12/2007 | |
| EP | 1476204 B1 | 10/2008 | |
| EP | 1433485 B1 | 11/2009 | |
| EP | 2259788 A2 | 12/2010 | |
| EP | 2379059 A1 | 10/2011 | |
| EP | 2402043 A1 | 1/2012 | |
| EP | 2411440 B1 | 2/2012 | |
| EP | 2788040 B1 | 10/2014 | |
| EP | 2231254 B9 | 4/2015 | |
| EP | 2860194 B1 | 4/2015 | |
| EP | 2911735 B1 | 9/2015 | |
| EP | 2793962 B1 | 4/2016 | |
| EP | 1912627 B1 | 8/2016 | |
| EP | 3065807 A1 | 9/2016 | |
| EP | 3119447 A1 | 1/2017 | |
| EP | 3148334 A1 | 4/2017 | |
| EP | 3234000 A1 | 10/2017 | |
| EP | 3242657 A1 | 11/2017 | |
| EP | 2437844 B1 | 5/2018 | |
| EP | 2919846 B1 | 4/2019 | |
| EP | 3419597 B1 | 12/2019 | |
| EP | 2776079 B1 | 4/2020 | |
| EP | 3057617 B1 | 4/2020 | |
| EP | 3706816 A1 | 9/2020 | |
| EP | 3052111 B1 | 12/2020 | |
| EP | 3746112 A1 | 12/2020 | |
| EP | 3750523 A1 | 12/2020 | |
| EP | 3750524 A1 | 12/2020 | |
| EP | 3791865 A1 | 3/2021 | |
| EP | 3810085 A1 | 4/2021 | |
| EP | 3810094 A1 | 4/2021 | |
| EP | 3810095 A1 | 4/2021 | |
| EP | 3810268 A1 | 4/2021 | |
| EP | 3917584 A1 | 12/2021 | |
| EP | 3924031 A1 | 12/2021 | |
| EP | 3937994 A1 | 1/2022 | |
| EP | 3941542 B1 | 1/2022 | |
| EP | 3974007 A1 | 3/2022 | |
| EP | 4031131 A1 | 7/2022 | |
| EP | 4045054 A1 | 8/2022 | |
| EP | 4048229 A1 | 8/2022 | |
| EP | 4048298 A1 | 8/2022 | |
| EP | 4087558 A1 | 11/2022 | |
| JP | 2011139881 A | 7/2011 | |
| JP | 2011139882 A | 7/2011 | |
| WO | 1989003232 A1 | 4/1989 | |
| WO | 2002020005 A1 | 3/2002 | |
| WO | 2002024248 A1 | 3/2002 | |
| WO | 2004030706 A2 | 4/2004 | |
| WO | 2004066875 A1 | 8/2004 | |
| WO | 2005018600 A2 | 3/2005 | |
| WO | 2005058200 A1 | 6/2005 | |
| WO | 2005092418 A1 | 10/2005 | |
| WO | WO-2005092419 A1 * | 10/2005 | ............... A61L 2/18 |
| WO | 2006002365 A2 | 1/2006 | |
| WO | 2012034032 A2 | 3/2012 | |
| WO | 2013049033 A1 | 4/2013 | |
| WO | 2014139809 A1 | 9/2014 | |
| WO | 2015074730 A1 | 5/2015 | |
| WO | 2015075841 A1 | 5/2015 | |
| WO | 2015089189 A2 | 6/2015 | |
| WO | 2015184365 A1 | 12/2015 | |
| WO | 2016159859 A1 | 10/2016 | |
| WO | 2016206701 A1 | 12/2016 | |
| WO | 2018053111 A1 | 3/2018 | |
| WO | 2018153514 A1 | 8/2018 | |
| WO | 2019104213 A1 | 5/2019 | |
| WO | WO-2019123005 A1 * | 6/2019 | |
| WO | 2021089470 A1 | 5/2021 | |
| WO | 2021168284 A1 | 8/2021 | |
| WO | 2022055559 A1 | 3/2022 | |
| WO | WO-2023211421 A1 * | 11/2023 | ........ A61M 25/0017 |

* cited by examiner

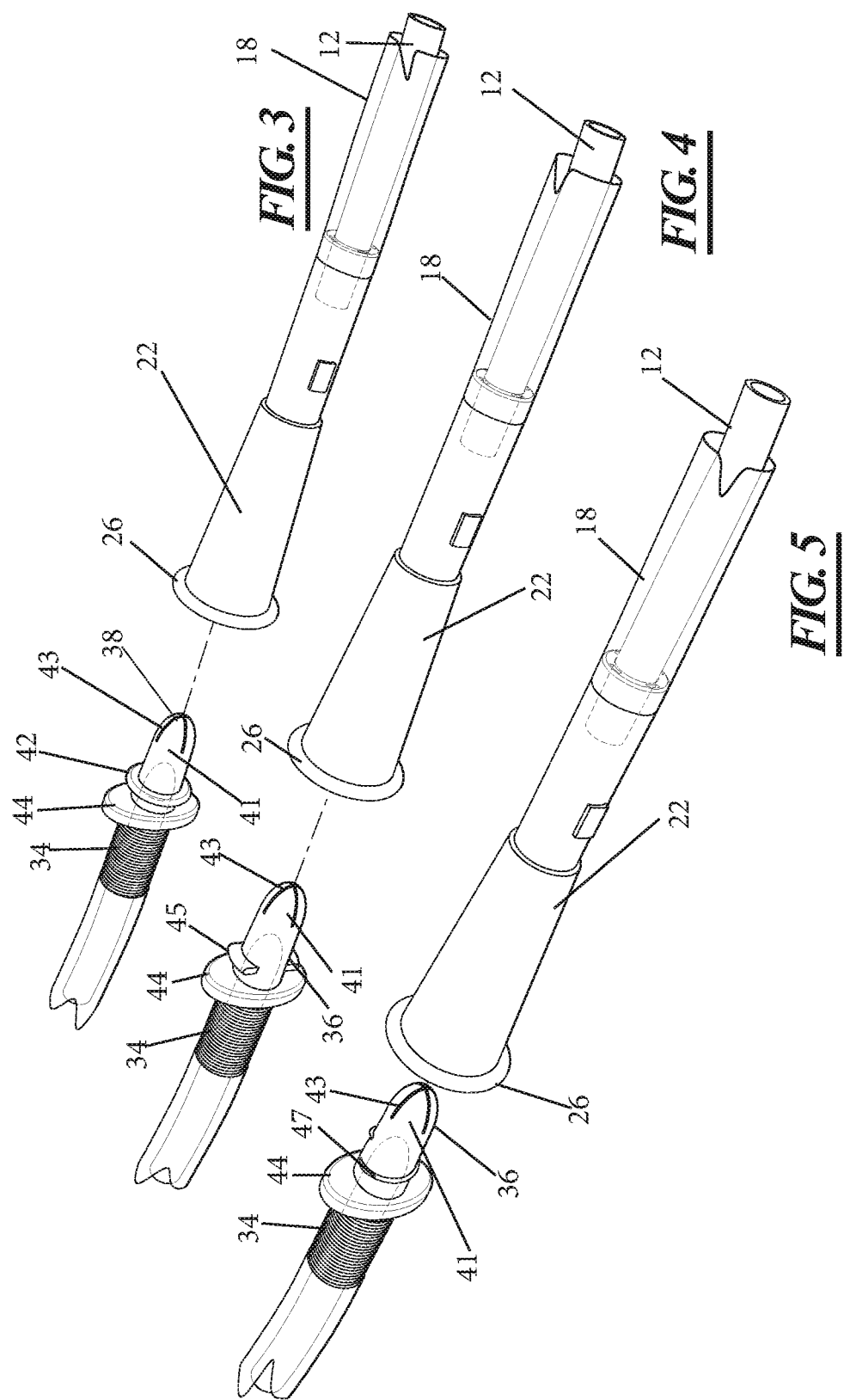

REUSABLE URINARY CATHETER PRODUCTS

CROSS-REFERENCE TO RELATED APPLICATION

This application is a National Stage Entry of International Application No. PCT/US2020/036969, filed Jun. 10, 2020, which claims the benefit of U.S. Provisional Application Ser. No. 62/861,130, filed Jun. 13, 2019, all of which are hereby incorporated by reference in their entirety.

BACKGROUND

Field of the Disclosure

The present disclosure generally relates to urinary catheters. More particularly, the present disclosure relates to reusable urinary catheter products.

Description of Related Art

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary retention or incontinence. With the advent of intermittent catheters, individuals with urinary system abnormalities can self-insert and self-remove intermittent catheters several times a day.

Urinary catheters are frequently provided as disposable, single-use items. A user will remove the catheter from a package, use the catheter once, and then dispose of the catheter and the package. Reusable urinary catheters could, thus, be advantageous in reducing the amount of waste created by the use disposable catheters, but there are various challenges associated with the use of reusable catheters (including storage, transport, and sterilization) that must be overcome before widespread acceptance and use of reusable catheters.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a reusable urinary catheter product includes a catheter tube having a proximal insertion end and a distal end. The product also includes a drainage member having a proximal end portion and a distal end portion. The proximal end portion of the drainage member is connected to the distal end of the catheter tube and the distal end portion of the drainage member defines a drainage opening. The product includes a collapsible sleeve surrounding the catheter tube such that the catheter tube is located within an interior cavity that is defined by the sleeve. The sleeve has a proximal end portion and a distal end portion. An introducer is attached to the proximal end portion of the sleeve and the distal end portion of the sleeve is attached to the drainage member, wherein the introducer is releasably attached to the drainage member. A sterilization fluid located within the interior cavity of the sleeve and the drainage member includes channels in fluid communication with the interior cavity of the sleeve. The channels allow passage of sterilization fluid into and out of the sleeve.

In another aspect, a reusable urinary catheter product includes a catheter tube having a proximal insertion end and a distal end. The product also includes a drainage member having a proximal end portion and a distal end portion. The proximal end portion of the drainage member is connected to the distal end of the catheter tube and the distal end portion of the drainage member defines a drainage opening. The product includes a collapsible sleeve surrounding the catheter tube such that the catheter tube is located within an interior cavity defined by the sleeve. The sleeve having a proximal end portion and a distal end portion. An introducer attached to the proximal end portion of the sleeve and the distal end portion of the sleeve is attached to the drainage member. The drainage member including channels in fluid communication with the interior cavity of the sleeve that allow passage of sterilization fluid into and out of the sleeve. A holder having a first port and a second port. The introducer is releasably attached to the first port and the drainage member is releasably attached to the second port. A sterilization fluid located within the sleeve.

BRIEF DESCRIPTION OF THE DRAWINGS

FIGS. 3-5 are perspective views showing various embodiments of connection elements of the introducer;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
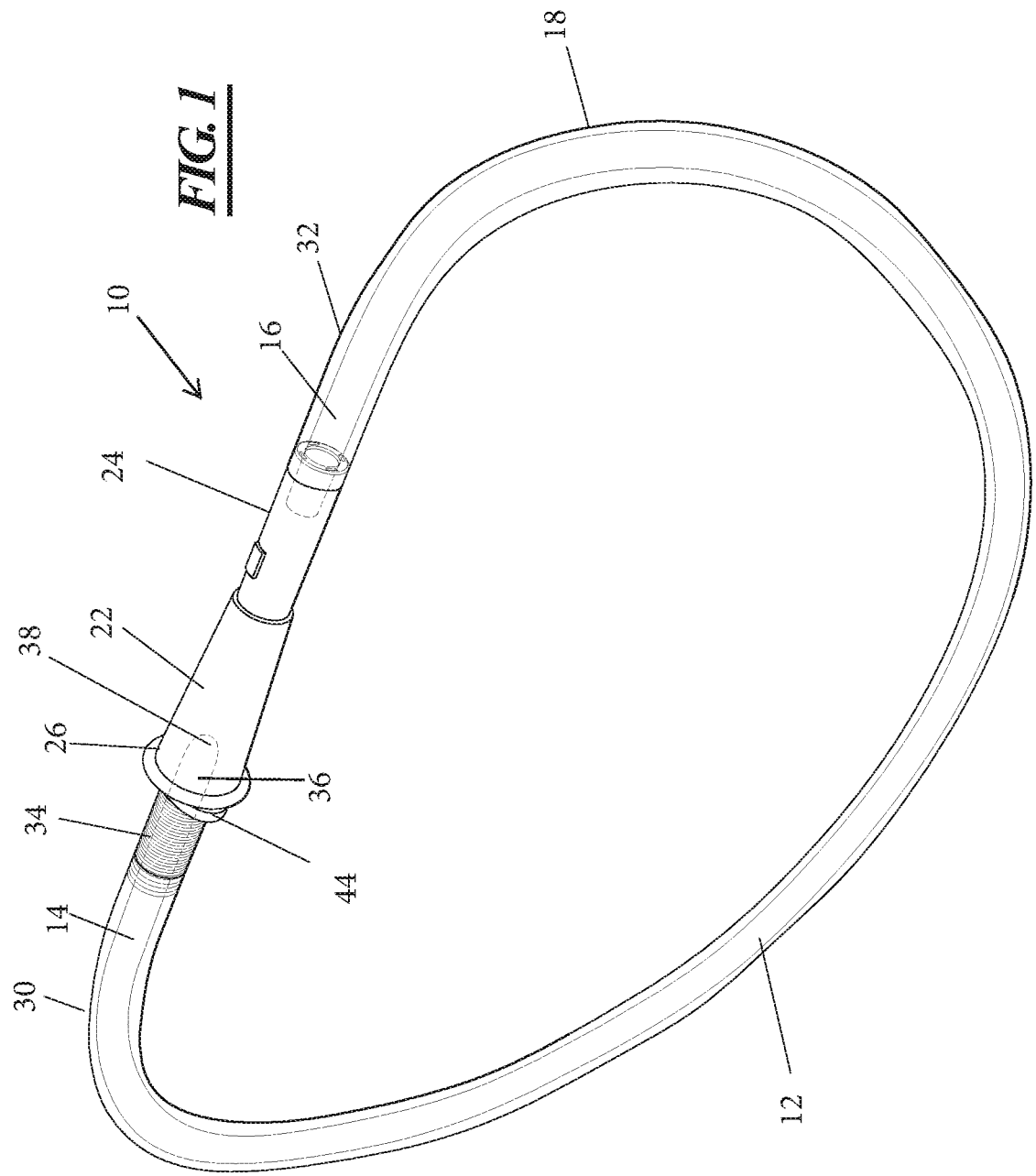
FIG. 1 is a perspective view of a reusable urinary catheter product according to an aspect of the present disclosure, with the catheter product in a closed loop configuration.

Reusable urinary catheter products according to the present disclosure and their individual components may be variously configured without departing from the scope of the present disclosure, but in one embodiment, a reusable urinary catheter product 10 is configured as shown in FIG. 1. In particular, the illustrated product 10 includes a catheter tube 12 having a proximal end portion 14 and a distal end portion 16. The product 10 also includes a sleeve 18 surrounding the catheter tube 12 wherein the catheter tube 12 is located within an interior cavity 20 defined by sleeve 18. Prior to use or between uses of the catheter product 10, a sterilization fluid may be located within the interior cavity 20 of the sleeve 18. The sterilization fluid contacts the catheter tube 12 and other elements of the catheter product 10 to sterilize the catheter product 10 prior to and/or between uses of the catheter product 10. As will be explained in more detail below, prior to preforming catheterization, the user drains the sterilization fluid from the catheter product 10. After the sterilization fluid has been drained, catheterization is performed. After catheterization, the user adds sterilization fluid to the catheter product 10 and stores the catheter product 10 until the next use.

Figure 2:
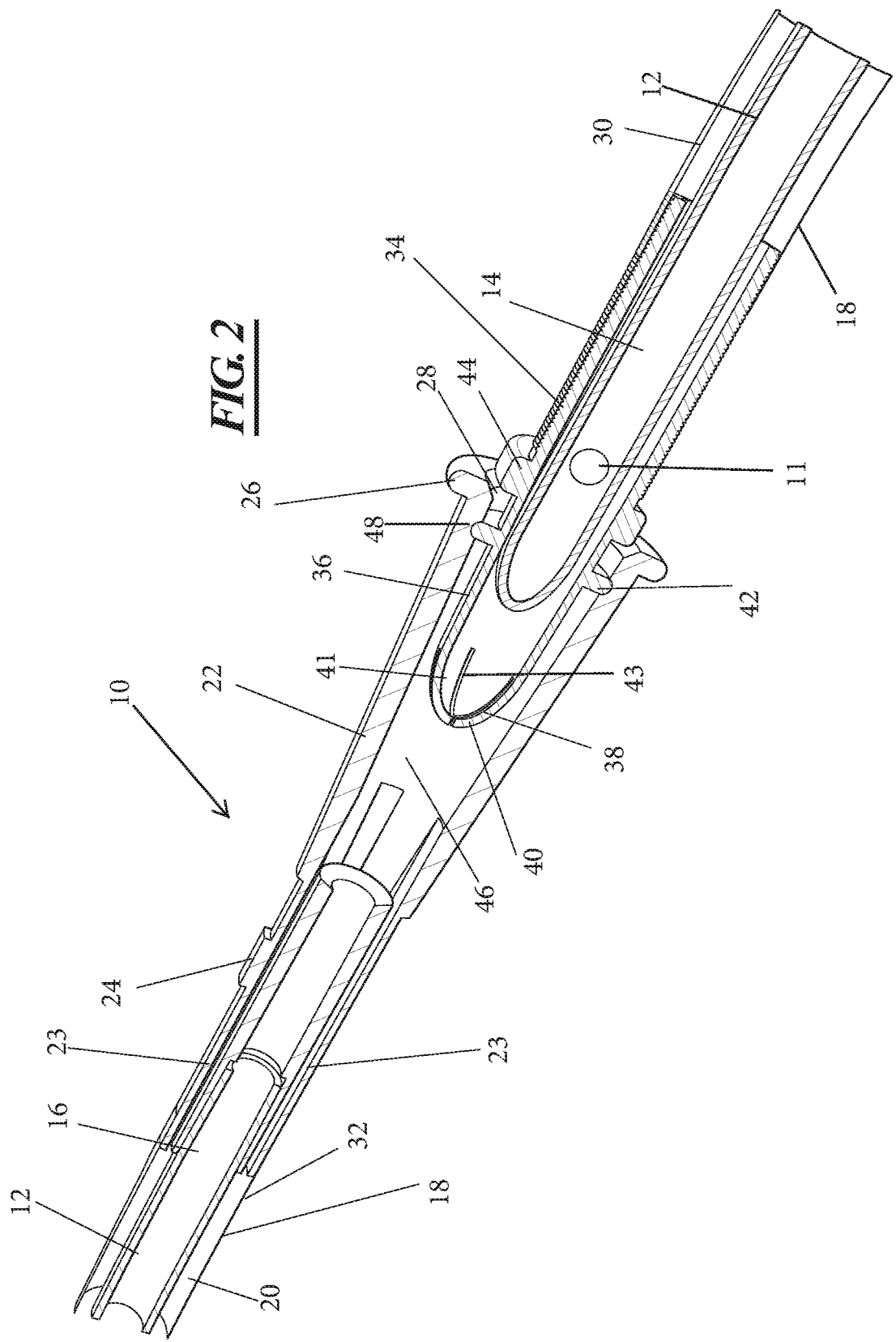
FIG. 2 is a partial cross-sectional view of the catheter product showing the connection between the drainage member and introducer.

Turning back to the catheter tube 12, the proximal end portion 14 of the catheter tube 12 includes openings or eyes 11 (FIG. 2) that allow liquid to flow therethrough. A drainage member 22 is associated with the distal end portion 16 of the catheter tube 12. The drainage member 22 may be a funnel and/or a connector that connects to a urine collection bag. The drainage member 22 includes a proximal end portion 24 attached to the distal end portion 16 of the catheter tube 12. A distal end portion 26 of the drainage member 22 defines a drainage opening 28 (FIGS. 2 and 6) for the drainage of fluids. Referring to FIG. 2, the drainage member 22 also includes one or more channels 23 in fluid communication with the cavity 20 of the sleeve 18. As will be explained in more detail below, the channels 23 allow the passage of sterilization fluid to and from the cavity 20 of sleeve 18. That is, the channels 23 allow fluid to be dispensed into the cavity 20, and also allow fluid to be drained from the cavity 20. In the illustrated embodiment, the channels 23 extend from the proximal end of the drainage member 22 and are in fluid communication with the drainage opening 28 in the distal end 26 of the drainage member 22.

As mentioned above, the sleeve 18 surrounds the catheter tube 12 such that the catheter tube 12 is located within an interior cavity 20 defined by the sleeve 18. The sleeve 18 includes a proximal end portion 30 and a distal end portion 32. The distal end portion 32 of the sleeve 18 is attached to the proximal end portion 24 of the drainage member 22. An introducer 34 is attached to the proximal end portion 30 of the sleeve 18. The proximal end portion 36 of the introducer 34 may include an introducer tip 38 which may be configured to be inserted into the urethral opening prior to insertion of the catheter tube 12. The introducer tip 38 may include an opening, which may be a reclosable opening 40. In the embodiments illustrated in FIGS. 2-5, the reclosable opening 40 includes a plurality of flexible petals 41 that are separated by slits 43. The petals 41 are flexible so as to allow advancement of the catheter tube 12 through opening 40 for insertion of the catheter tube 12 into the urethra. The petals 41 also allow retraction of the catheter tube 12 back into the sleeve 18, and the petals 41 are resilient so as to reclose opening 40 after the catheter has been fully retracted into sleeve 18. The introducer 34 also may include a stop or flange 42 that contacts the urinary meatus during insertion into the urethra to prevent over insertion of the introducer tip 38. The introducer 34 may include a second flange 44 that assists the user in placing the user's fingers in a position to grasping the catheter product 10.

As shown in FIGS. 1-5, the introducer 34 may be releasable connected or attached to the drainage member 22 so that the catheter product 10 forms in a closed loop configuration. The closed loop configuration could include one or multiple loops or windings. As illustrated in FIG. 2, when the introducer 34 includes an introducer tip 38, the introducer tip 38 may be inserted into the drainage opening 28 of the drainage member 22. The introducer 34 may contact the inner surface 46 of the drainage member 22 in a manner that forms a fiction fit or snap fit to releasable connect the drainage member 22 and the introducer 34 to each other. The connection between the drainage member 22 and introducer 34 is a liquid tight connection so that the sterilization fluid is contained within the catheter product during storage of the catheter product 10 between uses. Referring to FIG. 2, in the illustrated embodiment, the inner surface 46 of the drainage member 22 includes a groove or a recess 48 which mates with or accepts flange 42 of the introducer 34 to releasable secure the drainage member 22 and the introducer 34 together. Optionally, the flange 44 of the introducer 34 may contact or mate with the distal end portion 26 of the drainage member 22, about the area of the opening 28, to provide a liquid tight seal. When the introducer 34 includes an introducer tip 38, one of the benefits of this configuration is that the introducer tip is stored in and protected by the drainage member 22.

FIGS. 4 and 5 illustrate alternative embodiments of attachment mechanisms for releasably attaching the introducer 34 and the drainage member 22. In FIG. 4, the proximal end portion of the introducer 34 includes a plurality of protrusions or ribs 45. For example, the introducer 34 may include opposed protrusions or ribs 45. The protrusions 45 engage or mate with the inner surface of the drainage member 22 to secure the drainage member 22 and the introducer 34. Similar to as described above, the inner surface of the drainage member 22 may have a recess or groove that mate with the protrusions. Turning to FIG. 5, the proximal end 36 of the introducer 34 may include a thread 47 which mates with inner surface of the drainage member 22. The inner surface of the drainage member 22 may include a complementary threaded portion. The attachment mechanisms 42, 45 and 47 or any other suitable attachment mechanisms may be incorporated into the flange 44, instead of being on the insertion tip. Optionally, the flange could be eliminated the attachment mechanism could serve as a stop or flange that contacts the urethral opening.

As mentioned above, prior to use or while the reusable catheter product 10 is stored between uses, a sterilization fluid may be located in the interior cavity 20 of the sleeve 18. The sterilization fluid contacts the inner and outer surfaces of the catheter tube 12 and introducer 34 and the inner surfaces of the drainage member 22 to sterilize the catheter product 10 between uses. The sterilization fluid may be any suitable biocompatible sterilization fluid. Such fluids may include antimicrobial agents, such as agents that kill bacteria, viruses or other microbes, agents that prevent microbial growth, anti-adherence agents that prevent microbes from adhering to the surfaces, etc. Furthermore, when the catheter tube 12 is a hydrophilic catheter tube that has an outer hydrophilic surface that becomes lubricous when wetted or hydrated, the sterilization fluid may also serve has a hydration fluid that hydrates the hydrophilic surface. The lubricious hydrophilic outer surface assists in inserting the catheter into and retracting the catheter out of the urethra. In other embodiments, the sterilization fluid may include a lubricant, such as oil or water based lubricants that lubricates the outer surface. In yet other embodiments, the user may apply a lubricant just prior to use.

The sterilization fluids may also be a fluid that can be formed into a foam. Such fluids may include a surface tension reducing agent and a foam stabilization agent. The surface tension reducing agent may assist in adding or incorporating gas bubbles into the sterilization fluid to form a foam. In one embodiment, the surface tension reducing agent may be a surfactant or a mixture of surfactants. The surface tension reducing agent may be a foaming agent. The foam stabilizer may slow coalescence of the foam. In one embodiment, the sterilization fluid may include an antimicrobial agent and a surfactant (e.g., sodium dodecyl sulphate or sodium methyl cocoyl taurate) and a stabilizer (e.g., Xanthan gum). The sterilization fluid can be transformed into a foam by homogenizing air with the fluid. The air may be homogenized with the sterilization fluid by agitation of the fluid in the presence of air. The agitation can be a result of the user shaking the catheter product or a result of ordinary movement of the catheter product as the user carries it around. As disclosed in more detail below, in other embodiments, the catheter product may include an agitation mechanism, such as a pump, restriction, homogenizer, etc.

Figure 6:
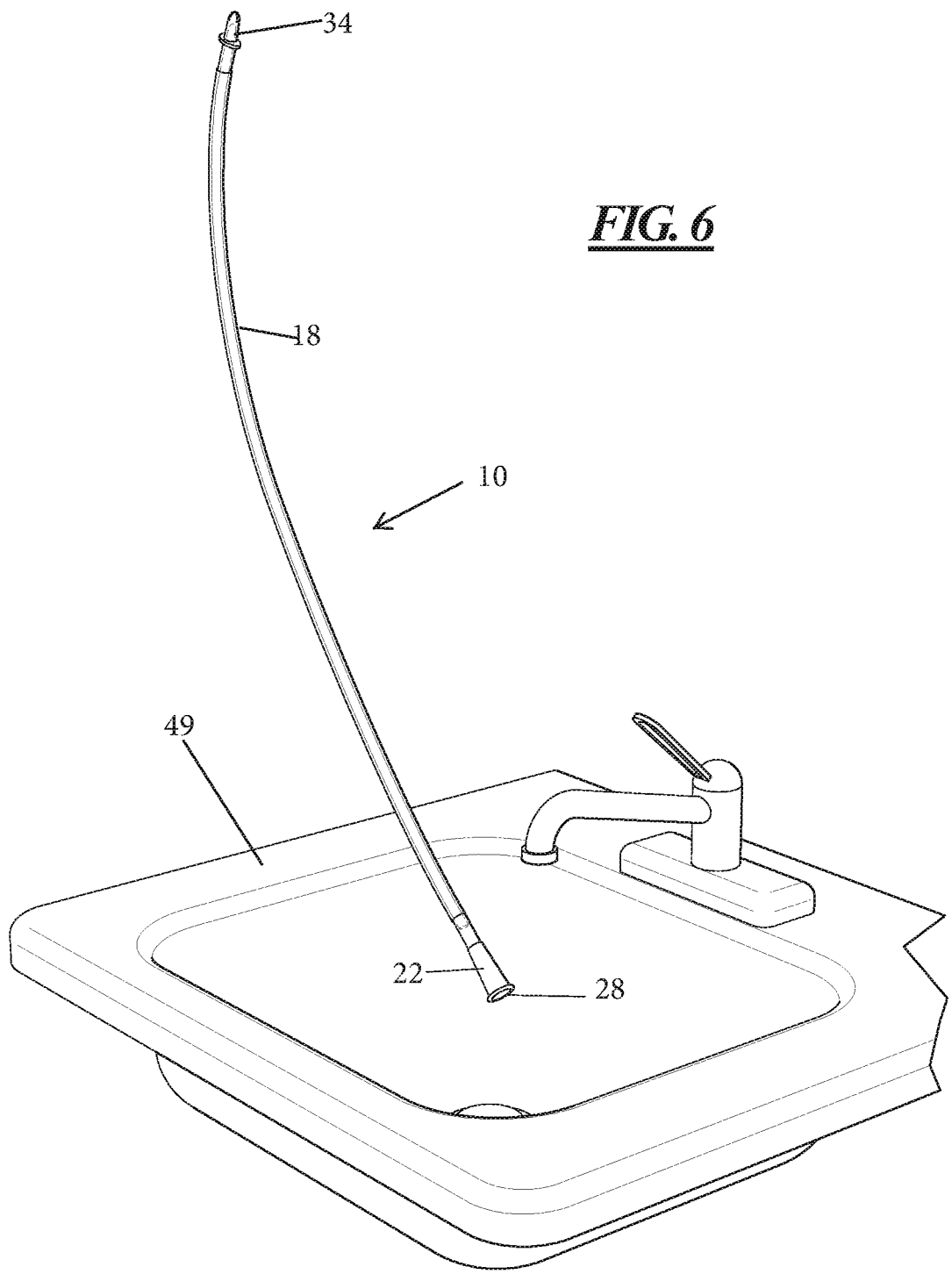
FIG. 6 is a perspective view the catheter product of FIG. 1, showing the catheter product in a generally straight configuration to allow drainage of the sterilization fluid from the catheter product.

Referring to FIGS. 6-9, in use, the user disengages the introducer 34 from the drainage member 22. The drainage member 22 is then held at a location that is lower than the introducer 34 to drain the sterilization fluid from the cavity of the sleeve 18. The sterilization fluid drains from the cavity of the sleeve 18 through channels 23 in the drainage member 22 (FIG. 2). In FIG. 6, the sterilization fluid is drained into a sink 49. Once the sterilization fluid has been sufficiently drained from the sleeve 18, the insertion tip 38 of the introducer 34, if one is present, is inserted into the urethra of the user. The user then proceeds to advance the catheter tube 12 out of the introducer 34 and into and through the urethra by grasping the catheter tube 12 through the sleeve 18. The sleeve 18 is flexible and collapsible such that it collapses as the catheter tube 12 is advanced. The catheter tube 12 is advanced through the urethra until the proximal end of the catheter tube 12 reaches the bladder. Urine is then drained from the bladder through the catheter tube 12.

Figure 7:
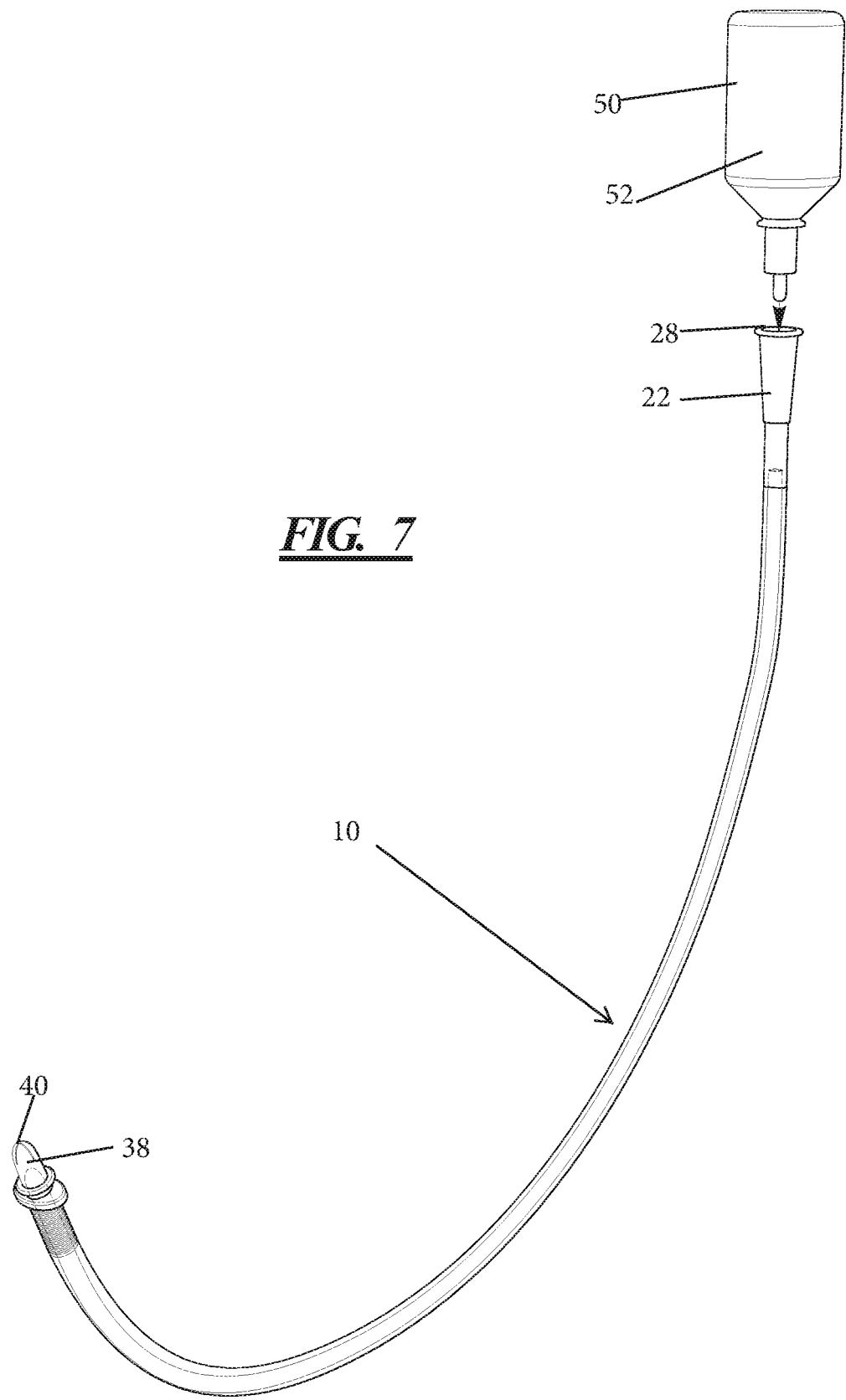
FIG. 7 is a perspective view of the catheter product of FIG. 1, with sterilization fluid being dispensed into the catheter product.
Figure 8:
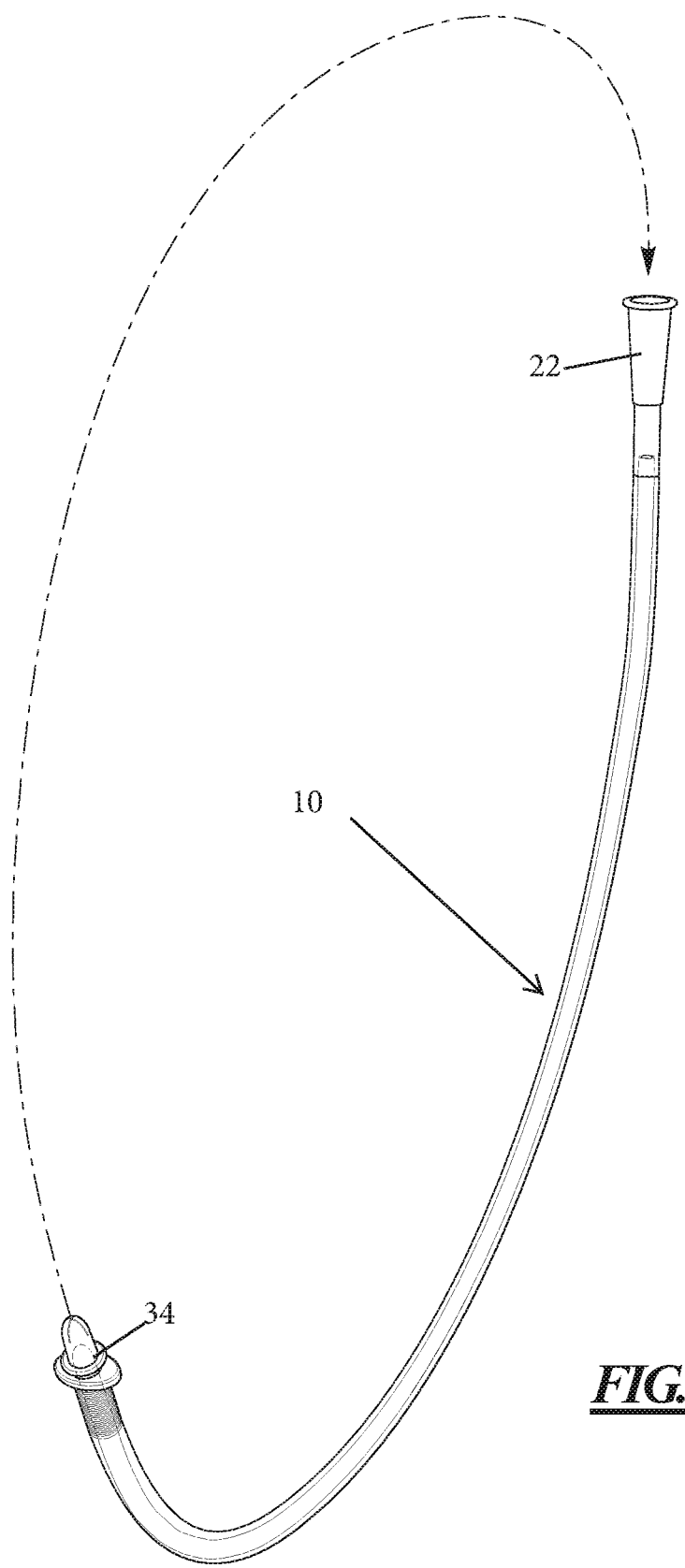
FIG. 8 is a perspective view of the catheter product of FIG. 1, illustrating the catheter product being placed back into the closed loop condition following use.
Figure 9:
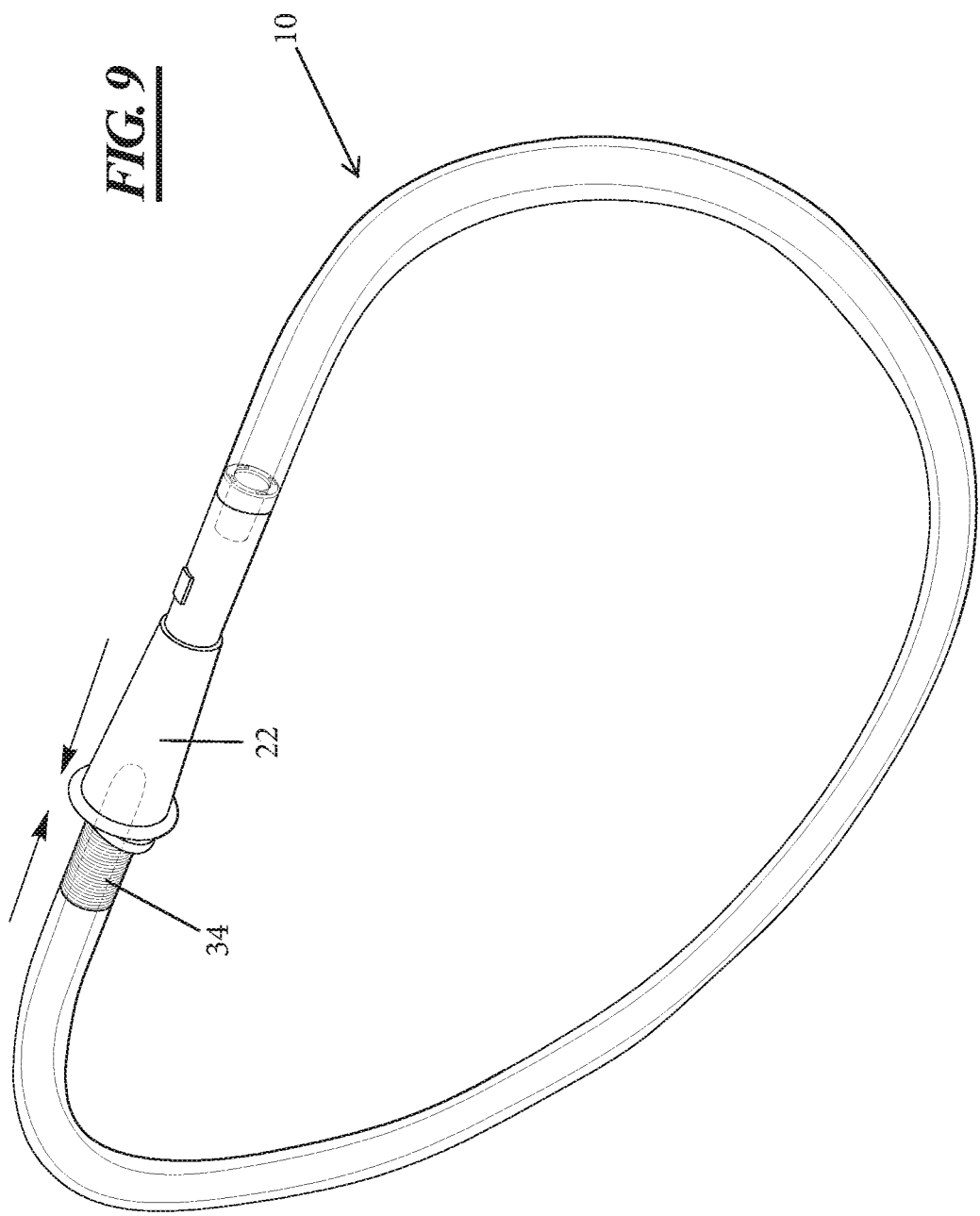
FIG. 9 is a perspective view of the catheter product of FIG. 1, with the drainage member being reconnected to the introducer to form the closed looped configuration for storage and sterilization.
Figure 10:
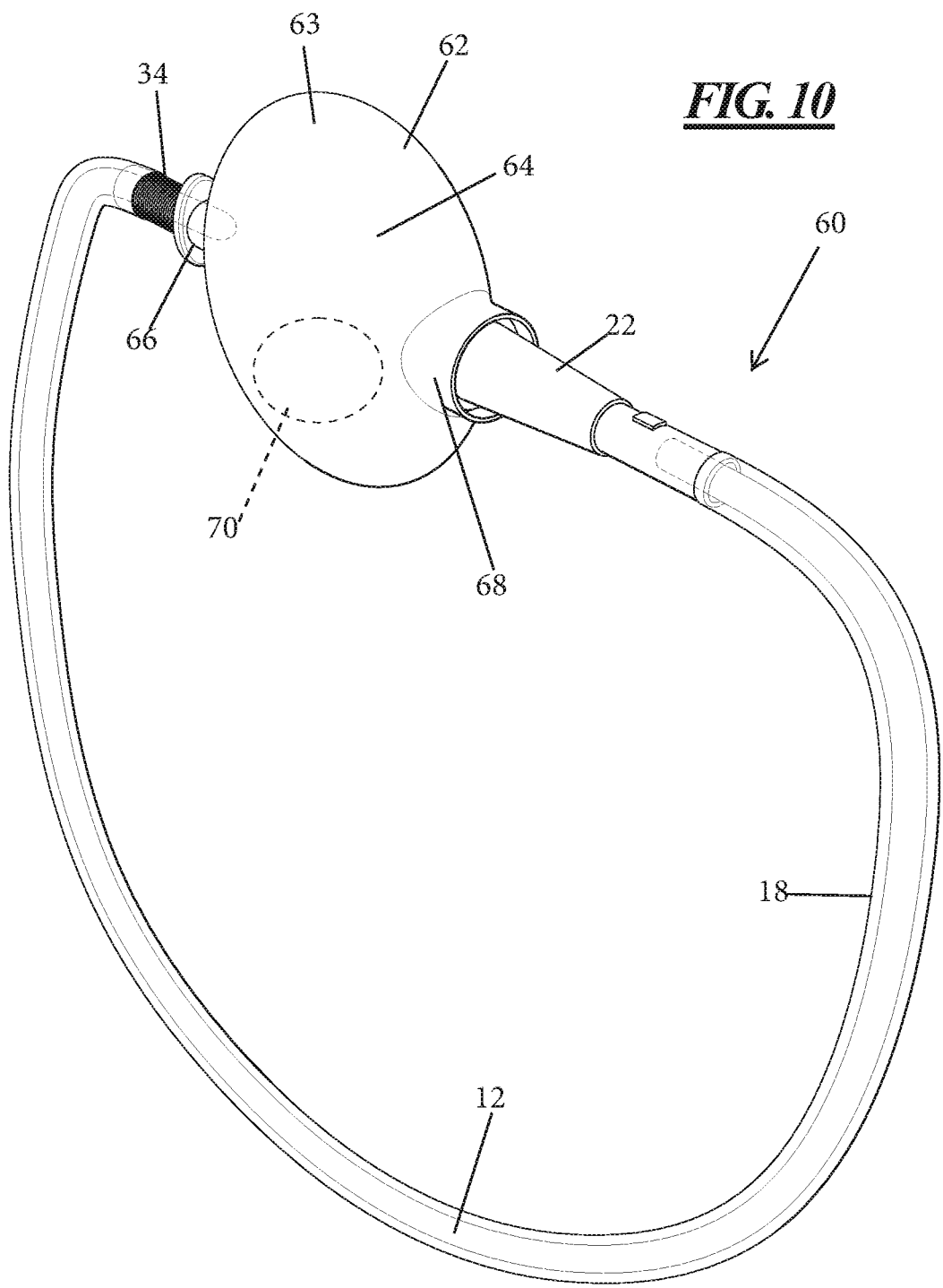
FIG. 10 is a perspective view of another embodiment of a reusable catheter product according to another aspect of the present disclosure.

After urine has been drained from the bladder, the catheter tube 12 is removed from the bladder. The catheter tube 12 is retracted back through the introducer 34 so that the sleeve 18 once again extends over the catheter tube 12 and the proximal end of the catheter tube 12 is within the introducer 34 and/or the cavity 20 of the sleeve 18. As shown in FIG. 7, a supply of sterilizing fluid 50 is used to add sterilizing fluid to the catheter product 10. In the illustrated embodiment, sterilizing fluid is dispensed from a bottle 52 into the drainage opening 28 of the drainage member 22. The fluid may travel through the channels 23 of the drainage member 22 (FIG. 2) and/or through the eyelet 11 of the catheter tube 12 (FIG. 2) into the cavity 20 defined by sleeve 18. As the fluid enters the cavity 20, the reclosable opening 40 of the introducer tip 38 prevents the fluid from exiting out of the proximal end of the sleeve 18 or catheter product 10. After a sufficient amount of sterilization fluid has been dispensed into the catheter product 10, the catheter product 10 is placed into the closed loop configuration by reattaching the introducer 34 to the drainage member 22 as shown in FIGS. 8 and 9. The catheter product 10 may be manually agitated (e.g., by shaking it) to circulate the sterilization fluid within the cavity of the sleeve 18. Agitation may also occur as the user carries the catheter with them during every day activities. When the fluid is one that forms a foam, as described above, manual agitation of the fluid results in foaming of the fluid. As shown in FIG. 2, when the introducer 34 is attached to the drainage member 22, the reclosable opening 40 of the introducer tip 38 serves as an obstruction and/or restriction in fluid path which prevents or restricts the movement of the sterilization fluid. In other embodiments, the introducer tip 38 may be always be open such that the fluid circulates within the closed looped configuration. When the fluid is agitated and the introducer tip includes a reclosable opening, the fluid sloshes against the introducer tip 38 so that the fluid moves move back and forth within the cavity. When a foaming sterilization fluid is used, this obstruction and/or restriction may assist in forming the fluid into a foam. When the user is ready to catheterize again, the user removes the introducer from the drainage member, drains the fluid from the product, and repeats the above discussed catheterization procedure.

FIGS. 10-13 illustrate embodiments wherein the catheter products 60 and 72 include a holder 62 and 74, respectively, that hold the catheters between uses. The catheter products 60 and 72 include several of the same components as catheter product 10 described above. For example, catheter products 60 and 72 include a catheter tube 12, sleeve 18, drainage member 22, introducer 34, etc. In the embodiment illustrated in FIGS. 10-12, the holder 62 may also serve as a pump for moving or agitating sterilization fluid within the catheter product 60. The holder 62 may be an elastic bulb 63 which can be repeatedly squeezed by the user to move and/or agitate sterilization fluid within the catheter product 60. The bulb 63 includes an inner chamber 64 and a first port 66 and a second port 68 that may be in communication with the inner chamber. The first port 66 is configured for releasable attachment to the introducer 34 and the second port 68 is configured for releasable attachment to the drainage member 22. The attachments between the ports 66, 68 and the introducer 34 and the drainage member 22 are preferably fluid tight attachments.

When the fluid is one that may be foamed, squeezing of the bulb 63 agitates the fluid, resulting in the formation of a foam from the fluid. In one alternative embodiment, a sponge 70 may be located within the bulb. When the bulb is compressed, the sponge is also compressed, which may aid in adding air to the fluid. One or both of the ports 66, 68 may include restrictions or obstructions or one way valves, which also may assist in foaming the fluid. For embodiments in which a sterilization fluid is circulated through the kit, the fluid path may include one or more filters or screens configured to entrap debris circulating through the fluid path. Each filter or screen may be placed in any suitable location within the fluid path and may be variously configured without departing from the scope of the present disclosure. In an exemplary embodiment, the filter or screen may be provided as a flat mesh with pores that are sized and configured to entrap particulates that may be present in urine. In other embodiments, the filter or screen may be differently configured (e.g., being formed of a woven or non-woven material), including having any pore size and/or porosity. If multiple filters or screens are provided, they may be substantially identical or differently configured and may be positioned at any suitable location with respect to each other. In one embodiment, the filter or screen may be placed in the return loop returning fluid to the pump for recycling.

In this embodiment, the filter entraps debris prior to the fluid entering the pump and being returned back into the compartment with the catheter.

Figure 11:
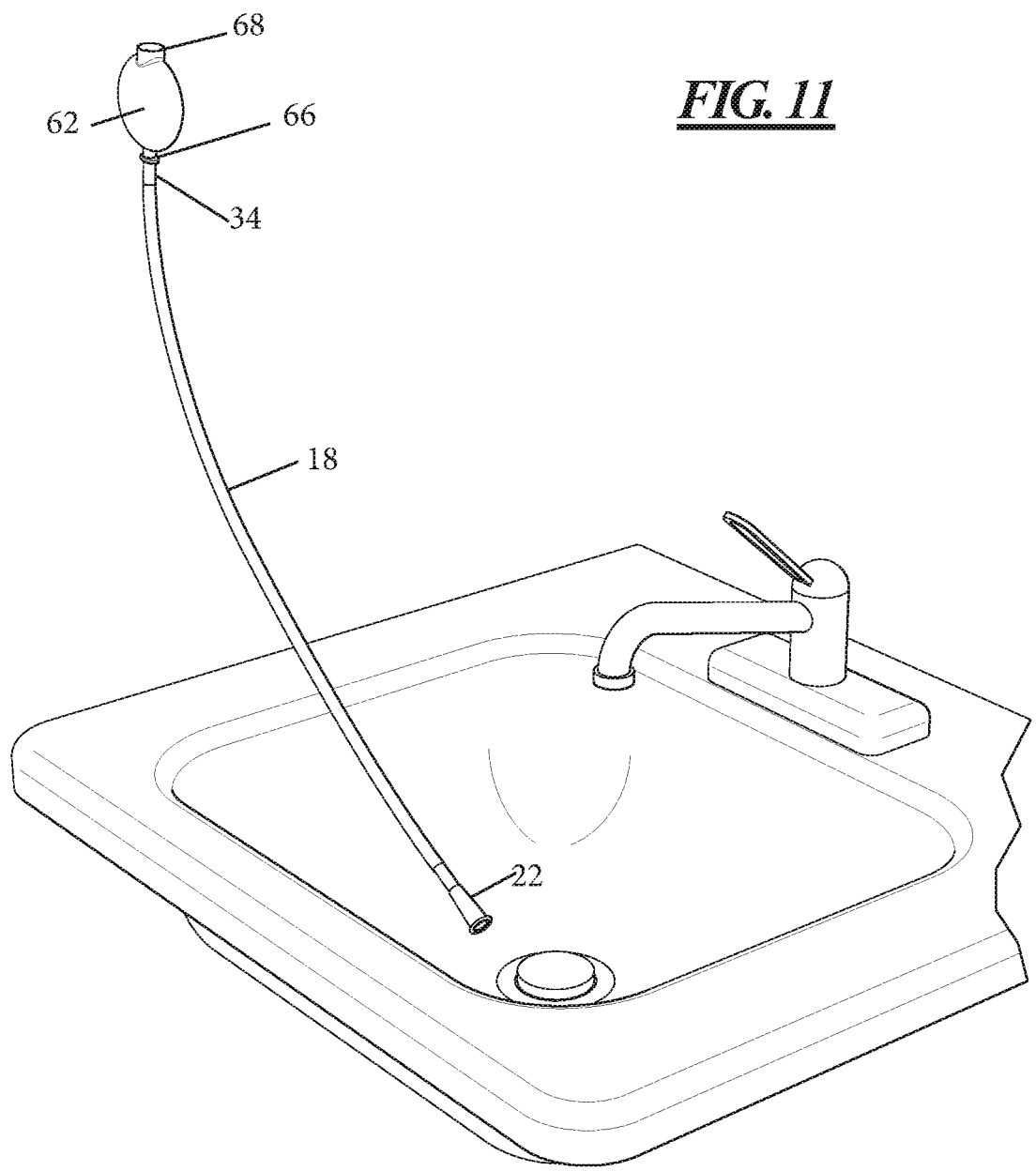
FIG. 11 is a perspective view the catheter product of FIG. 10, showing the catheter product in a generally straight configuration to allow drainage of the sterilization fluid from the catheter product.
Figure 12:
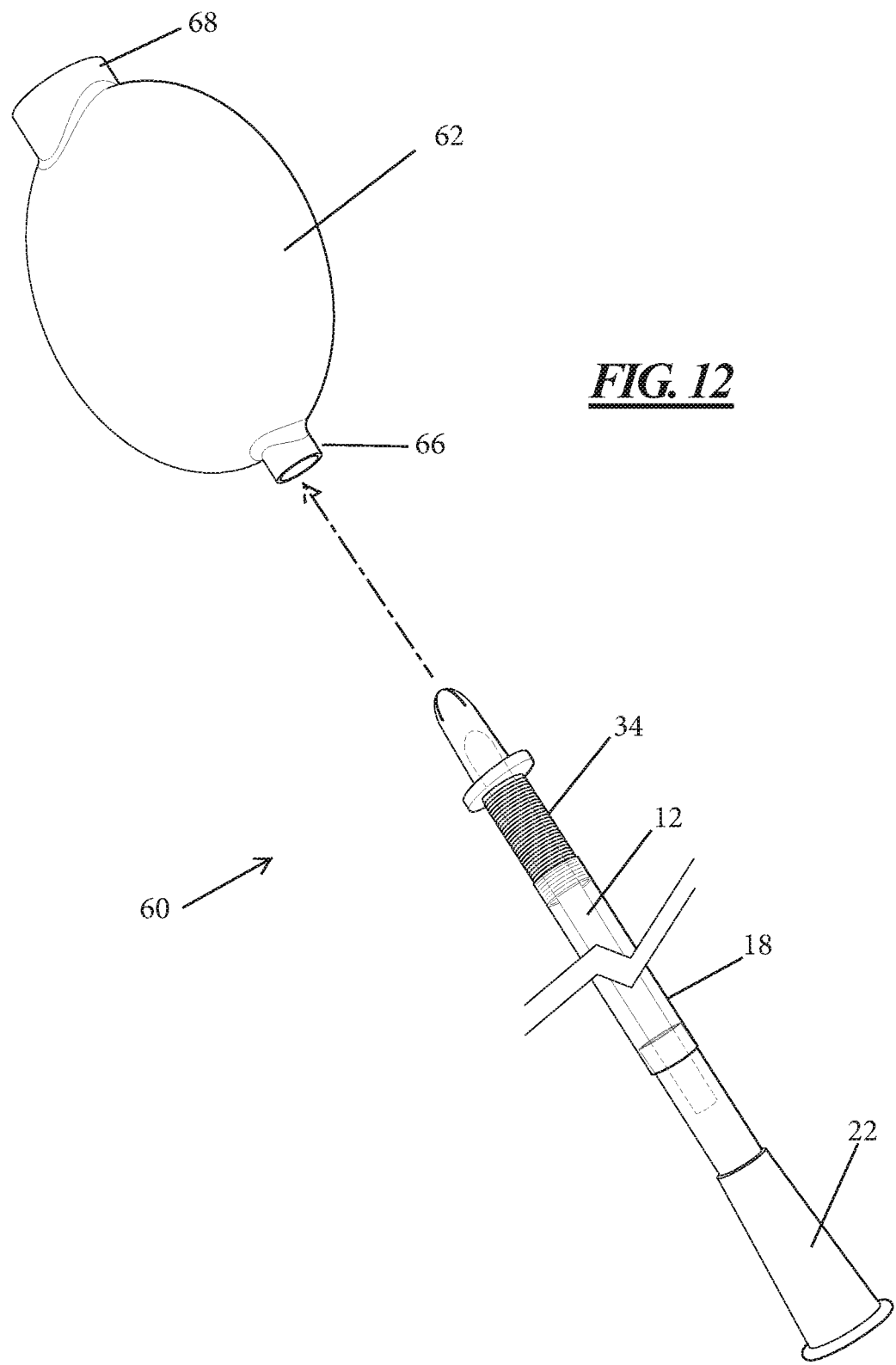
FIG. 12 is a perspective view of the catheter product of FIG. 10, illustrating the introducer being reattached to the holder.

Referring to FIG. 11, in use, the drainage member 22 is detached from port 68 of the holder 62 and placed below the introducer 34. The sterilization fluid is drained from the cavity of the sleeve 18 as described above. The introducer 34 is detached from the holder 62 and catheterization is performed as described above. The catheter tube is then retracted back into the introducer and the sleeve once again extends over the catheter tube. Referring to FIG. 12, the introducer 34 may be reattached to the port 66. Sterilization fluid (not shown) may be dispensed into the holder 62 through port 68. The drainage member 22 may then be reattached to port 68. The user may then compress holder 62 to agitate the fluid within the catheter product 60. The sterilization fluid sterilizes the catheter product 60 so it is ready for use the next time the user requires catheterization.

Figure 13:
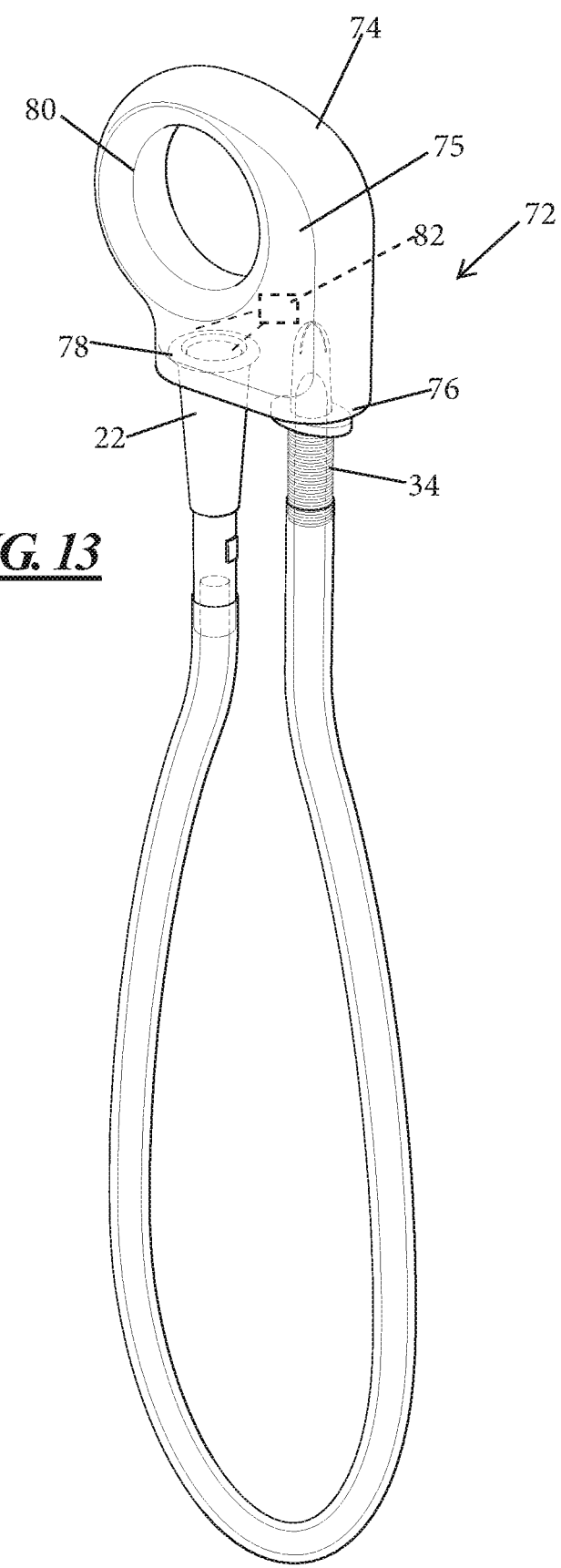
FIG. 13 is a perspective view of another embodiment of a reusable catheter product according to another aspect of the present disclosure.

FIG. 13 illustrates another embodiment of a catheter product 72 that is includes a holder 74. The holder 74 includes a body 75 having a first port 76 configured for releasable attachment to the introducer 34 and a second port 78 configured for releasable attachment to drainage member 22. The attachments between the ports 76 and 78 and the introducer 34 and drainage member 22 are liquid tight. The body 75 may also include a ring shaped portion 80 that may be used to grasp the catheter product. The holder 74 may also include an electric pump or agitator 82 associated with the port 78 and in fluid communication with drainage member 22. When the drainage member 22 and introducer 34 are attached to their respective ports, the electric pump or agitator may move or agitate the liquid within the catheter product 72.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A reusable urinary catheter product, comprising:
 a catheter tube having a proximal insertion end and a distal end;
 a drainage member having a proximal end portion and a distal end portion, the proximal end portion of the drainage member being connected to the distal end of the catheter tube, the distal end portion of the drainage member defining a drainage opening;
 a collapsible sleeve surrounding the catheter tube such that the catheter tube is located within an interior cavity defined by the sleeve, the sleeve having a proximal end portion and a distal end portion, an introducer attached to the proximal end portion of the sleeve and the distal end portion of the sleeve being attached to the drainage member, the drainage member including channels in fluid communication with the interior cavity of the sleeve, the channels allowing passage of sterilization fluid into and out of the sleeve;
 a holder having an inner chamber, a first port, and a second port, wherein the first port and second port are in communication with the inner chamber, a proximal end of the introducer being releasably attached to the first port, wherein the introducer is directly coupled within the first port, and a distal end of the drainage member being releasably attached to the second port, wherein the drainage member is directly coupled within the second port; and
 wherein a sterilization fluid flows through the inner chamber of the holder and interior cavity of the sleeve.

2. The reusable urinary catheter product of claim 1, wherein the holder is at least partially compressible.

3. The reusable urinary catheter product of claim 2, wherein the holder comprises a bulb, wherein when the bulb is compressed, the sterilization fluid is agitated and moved through the sleeve.

4. The reusable urinary catheter product of claim 3, wherein a sponge is located within the chamber of the holder.

5. The reusable urinary catheter product of claim 1, wherein the catheter tube includes a lubricious hydrophilic outer surface and the sterilization fluid hydrates the lubricious hydrophilic outer surface.

6. The reusable urinary catheter product of claim 1, wherein the sterilization fluid includes a lubricant.

7. The reusable urinary catheter product of claim 1, wherein the sterilization fluid comprises a foam.

8. The reusable urinary catheter product of claim 1, wherein fluid moves in a closed fluid path when the holder is compressed.

9. A reusable urinary catheter product, comprising:
 a catheter tube having a proximal insertion end and a distal end;
 a drainage member having a proximal end portion and a distal end portion, the proximal end portion of the drainage member being connected to the distal end of the catheter tube, the distal end portion of the drainage member defining a drainage opening;
 a collapsible sleeve surrounding the catheter tube such that the catheter tube is located within an interior cavity defined by the sleeve, the sleeve having a proximal end portion and a distal end portion, an introducer attached to the proximal end portion of the sleeve and the distal end portion of the sleeve being attached to the drainage member, the drainage member including channels in fluid communication with the interior cavity of the sleeve, the channels allowing passage of sterilization fluid into and out of the sleeve;
 a holder having a first port and a second port, a proximal end of the introducer being releasably attached to the first port, wherein the introducer is directly coupled within the first port, and a distal end of the drainage member being releasably attached to the second port, wherein the drainage member is directly coupled within the second port; and
 a sterilization fluid within the interior cavity of the sleeve.

10. The reusable urinary catheter product of claim 9, wherein the holder includes an electric pump or agitator for moving or agitating the sterilization fluid within the sleeve.

11. The reusable urinary catheter product of claim 9, wherein the holder is at least partially compressible.

12. The reusable urinary catheter product of claim 9, wherein the holder comprises a bulb, wherein when the bulb is compressed, the sterilization fluid is agitated and moved through the sleeve.

13. The reusable urinary catheter product of claim 9, wherein a sponge is located within a chamber of the holder.

14. The reusable urinary catheter product of claim 9, wherein the catheter tube includes a lubricious hydrophilic outer surface and the sterilization fluid hydrates the lubricious hydrophilic outer surface.

15. The reusable urinary catheter product of claim 9, wherein the holder includes a body having a ring shaped portion.

16. The reusable urinary catheter product of claim 9, wherein the sterilization fluid includes a lubricant.

17. The reusable urinary catheter product of claim 9, wherein the sterilization fluid comprises a foam.

18. The reusable urinary catheter product of claim 9, wherein fluid moves in a closed fluid path when the holder is compressed.

* * * * *